US008525875B2

(12) United States Patent
Kawata et al.

(10) Patent No.: US 8,525,875 B2
(45) Date of Patent: Sep. 3, 2013

(54) ADAPTER FOR ENDOSCOPE, PROCESSOR FOR ENDOSCOPE AND ENDOSCOPE SYSTEM

(71) Applicant: Olympus Medical Systems Corp., Tokyo (JP)

(72) Inventors: Susumu Kawata, Hachioji (JP); Takahiro Tanabe, Tachikawa (JP); Kazuma Kaneko, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/688,870

(22) Filed: Nov. 29, 2012

(65) Prior Publication Data

US 2013/0141557 A1    Jun. 6, 2013

Related U.S. Application Data

(63) Continuation of application No. PCT/JP2011/076509, filed on Nov. 17, 2011.

(30) Foreign Application Priority Data

Mar. 29, 2011 (JP) .................................. 2011-073370

(51) Int. Cl.
H04N 7/18    (2006.01)
(52) U.S. Cl.
USPC ........................................................ 348/65
(58) Field of Classification Search
USPC ........................................................ 348/56
See application file for complete search history.

(56) References Cited

U.S. PATENT DOCUMENTS

| 4,816,909 A | 3/1989 | Kimura et al. |
| 2007/0233888 A1 | 10/2007 | Yamaki |
| 2007/0244366 A1* | 10/2007 | Murata .......................... 600/175 |

FOREIGN PATENT DOCUMENTS

| EP | 1 835 427 A2 | 9/2007 |
| JP | 64-043227 A | 2/1989 |
| JP | 05-176886 A | 7/1993 |
| JP | 07-000360 A | 1/1995 |
| JP | 2007-244516 A | 9/2007 |
| JP | 2008-245934 A | 10/2008 |

OTHER PUBLICATIONS

International Search Report dated Jan. 17, 2012 issued in PCT/JP2011/076509.

* cited by examiner

Primary Examiner — Jayanti K Patel
Assistant Examiner — Yulin Sun
(74) Attorney, Agent, or Firm — Scully, Scott, Murphy & Presser, P.C.

(57) ABSTRACT

An adapter for endoscope includes: an image pickup device driving signal generation circuit; an image signal output circuit; an endoscope identification information reception circuit receiving endoscope ID information; a ROM storing adapter ID information about the adapter; a flash memory storing parameters for adjustment; and a control section performing control to store the parameters for adjustment into the flash memory according to a command from a processor to write the parameters for adjustment, and read the parameters for adjustment stored in the flash memory and output the parameters for adjustment stored in the flash memory to the processor according to a command from the processor to read the parameters for adjustment.

9 Claims, 6 Drawing Sheets

FIG.7

| ENDOSCOPE ID INFORMATION |
|---|
| ENDO1SN0001 |
| ENDO1SN0010 |
| ENDO1SN0002 |
| ENDO1SN0022 |
| ⋮ |

TBL1

FIG.8

| COMBINATION | ADAPTER ID INFORMATION | ENDOSCOPE ID INFORMATION |
|---|---|---|
| 1 | ADP1ZZ0001 | ENDO2SN0100 |
| 2 | ADP1ZZ0001 | ENDO2SN0111 |
| 3 | ADP2ZZ0010 | ENDO2SN0033 |
| 4 | ADP2ZZ0010 | ENDO2SN0100 |
| ⋮ | ⋮ | ⋮ |

TBL2

ADAPTER FOR ENDOSCOPE, PROCESSOR FOR ENDOSCOPE AND ENDOSCOPE SYSTEM

CROSS REFERENCE TO RELATED APPLICATION

This application is a continuation application of PCT/JP2011/076509 filed on Nov. 17, 2011 and claims benefit of Japanese Application No. 2011-073370 filed in Japan on Mar. 29, 2011, the entire contents of which are incorporated herein by this reference.

BACKGROUND OF THE INVENTION

1. Field of the Invention

The present invention relates to an adapter for endoscope, a processor for endoscope and an endoscope system.

2. Description of the Related Art

Conventionally, an endoscope system has been widely used in a medical field and an industrial field. The endoscope system makes it possible to perform observation, image recording and the like of an endoscopy target site by inserting an endoscope insertion portion of the endoscope system into an inside of a patient's body cavity or into an inside of an endoscopy object.

When a detachable endoscope is connected to a processor, the processor generates a driving signal for driving an image pickup device provided at a distal end portion of the endoscope insertion portion, performs image processing of an image signal, which is a video signal from the image pickup device, and displays an endoscopic image on a monitor. At that time, the processor cannot generate an appropriate endoscopic image without performing white balance adjustment of the endoscopic image. That is, the processor can generate an appropriate endoscopic image and output the endoscopic image on the monitor by obtaining various parameters for adjustment including a coefficient for white balance adjustment and the like, driving the endoscope on the basis of the parameters for adjustments and performing image processing of a received image signal.

For example, as shown in Japanese Patent Application Laid-Open Publication No. 05-176886, an endoscope apparatus is proposed which enables an endoscope holding parameters for adjustment, such as various gains, as respective resistance values of variable resistors to be connected to a processor via an adapter. The processor reads the resistance value via the adapter, discriminates parameters for adjustment from the resistance value, and performs driving and image processing of each endoscope on the basis of the discriminated various parameters for adjustment.

Recently, a new type of endoscope has been also proposed which includes a rewritable nonvolatile memory which stores the various parameters for adjustment.

According to the new type of endoscope which stores the various parameters for adjustment, according to the proposal, a processor identifies the endoscope on the basis of identification information about the endoscope connected, and performs various adjustments such as white balance adjustment if the identified endoscope is an endoscope connected for the first time. The processor obtains the various parameters for adjustment then and stores the various parameters for adjustment into the nonvolatile memory of the endoscope.

In the case of using the endoscope with such a configuration in combination with the processor, the processor judges whether or not the endoscope is an endoscope which has been previously connected when the endoscope is connected. If the endoscope is an endoscope which has been previously connected, the processor reads the various parameters for adjustment from the endoscope and uses the parameters for driving an image pickup device, image processing of an image signal and the like. Thus, after performing white balance adjustment and the like once, a user is not required to perform adjustment works such as white balance adjustment each time he uses the endoscope afterwards.

SUMMARY OF THE INVENTION

An adapter for endoscope according to an aspect of the present invention is an adapter for endoscope connecting an endoscope provided with an image pickup device which analog signals are inputted to and outputted from and a processor which digital signals are inputted to and outputted from; and the adapter is provided with: an image pickup device driving signal generation circuit generating a driving signal for driving the image pickup device on the basis of a driving control signal from the processor; an image signal output circuit converting an analog image signal from the image pickup device to a digital image signal in a serial signal format and outputting the digital image signal to the processor; an endoscope identification information reception circuit receiving endoscope identification information which is identification information about the endoscope; an adapter identification information storage section storing adapter identification information which is identification information about the adapter for endoscope; an information transmission section transmitting the endoscope identification information and the adapter identification information to the processor; a parameter-for-adjustment storage section storing parameters for adjustment; and a control section performing control to store the parameters for adjustment received from the processor into the parameter-for-adjustment storage section according to a command to write the parameters for adjustment from the processor which is configured to receive the endoscope identification information and the adapter identification information, and read the parameters for adjustment stored in the parameter-for-adjustment storage section according to a command to read the parameters for adjustment from the processor and output the parameters for adjustment to the processor.

A processor for endoscope according to an aspect of the present invention is a processor capable of inputting and outputting digital signals to and from an adapter for endoscope to which an endoscope is connectable, the endoscope being provided with an image pickup device which analog signals are inputted to and outputted from, wherein the adapter for endoscope comprises: an image pickup device driving signal generation circuit generating a driving signal for driving the image pickup device on the basis of a driving control signal from the processor; an image signal output circuit converting an analog image signal from the image pickup device to a digital image signal in a serial signal format and outputting the digital image signal to the processor; an endoscope identification information reception circuit receiving endoscope identification information which is identification information about the endoscope; an adapter identification information storage section storing adapter identification information which is identification information about the adapter for endoscope; an information transmission section transmitting the endoscope identification information and the adapter identification information to the processor; a parameter-for-adjustment storage section storing parameters for adjustment; and a control section performing control to store the parameters for adjustment received from the processor into the parameter-for-adjustment storage section according to a command to write the parameters for adjustment from the processor which is configured to receive the endoscope identification information and the adapter identification information, and read the parameters for adjustment stored in the parameter-for-adjustment storage section according to a command to read the parameters for adjustment from the processor and output the parameters for adjustment to the processor; and the processor comprises: an adjusted combination information storage section storing adjusted combination information showing whether predetermined adjustment processing has been performed or not for a combination of the endoscope identification information and the adapter identification information; and a control section judging existence or nonexistence of the adjusted combination information about a combination of the endoscope identification information and the adapter identification information received from the adapter for endoscope by referring to the adjusted combination information storage section; if the adjusted combination information does not exist, executing the predetermined adjustment processing, storing the parameters for adjustment obtained by the execution into the parameter-for-adjustment storage section of the adapter for endoscope and storing the adjusted combination information about the combination of the endoscope identification information and the adapter identification information into the adjusted combination information storage section; and, if the adjusted combination information exists, reading the parameters for adjustment stored in the parameter-for-adjustment storage section of the adapter for endoscope.

An endoscope system according to an aspect of the present invention is an endoscope system comprising: an adapter for endoscope to which an endoscope is connectable, the endoscope being provided with an image pickup device which analog signals are inputted to and outputted from; and a processor which digital signals are inputted to and outputted from, wherein the adapter for endoscope comprises: an image pickup device driving signal generation circuit generating a driving signal for driving the image pickup device on the basis of a driving control signal from the processor; an image signal output circuit converting an analog image signal from the image pickup device to a digital image signal in a serial signal format and outputting the digital image signal to the processor; an endoscope identification information reception circuit receiving endoscope identification information which is identification information about the endoscope; an adapter identification information storage section storing adapter identification information which is identification information about the adapter for endoscope; an information transmission section transmitting the endoscope identification information and the adapter identification information to the processor; a parameter-for-adjustment storage section storing parameters for adjustment; and a control section performing control to store the parameters for adjustment received from the processor into the parameter-for-adjustment storage section according to a command to write the parameters for adjustment from the processor which is configured to receive the endoscope identification information and the adapter identification information, and read the parameters for adjustment stored in the parameter-for-adjustment storage section according to a command to read the parameters for adjustment from the processor and output the parameters for adjustment to the processor; and the processor comprises: an adjusted combination information storage section storing adjusted combination information showing whether predetermined adjustment processing has been performed or not for a combination of the endoscope identification information and the adapter identification information; and a control section judging existence or nonexistence of the adjusted combination information about a combination of the endoscope identification information and the adapter identification information received from the adapter for endoscope by referring to the adjusted combination information storage section; if the adjusted combination information does not exist, executing the predetermined adjustment processing, storing the parameters for adjustment obtained by the execution into the parameter-for-adjustment storage section of the adapter for endoscope and storing the adjusted combination information about the combination of the endoscope identification information and the adapter identification information into the adjusted combination information storage section; and, if the adjusted combination information exists, reading the parameters for adjustment stored in the parameter-for-adjustment storage section of the adapter for endoscope.

BRIEF DESCRIPTION OF THE DRAWINGS

FIG. 7 is a diagram showing a configuration of a table for storing adjusted endoscope information about endoscopes 21 of a first type, according to the embodiment of the present invention;

FIG. 8 is a diagram showing a configuration of a table for storing adjusted combination information about endoscopes 31 of a second type and the adapters 41, according to the embodiment of the present invention;

DETAILED DESCRIPTION OF THE PREFERRED EMBODIMENT

Figure 1:
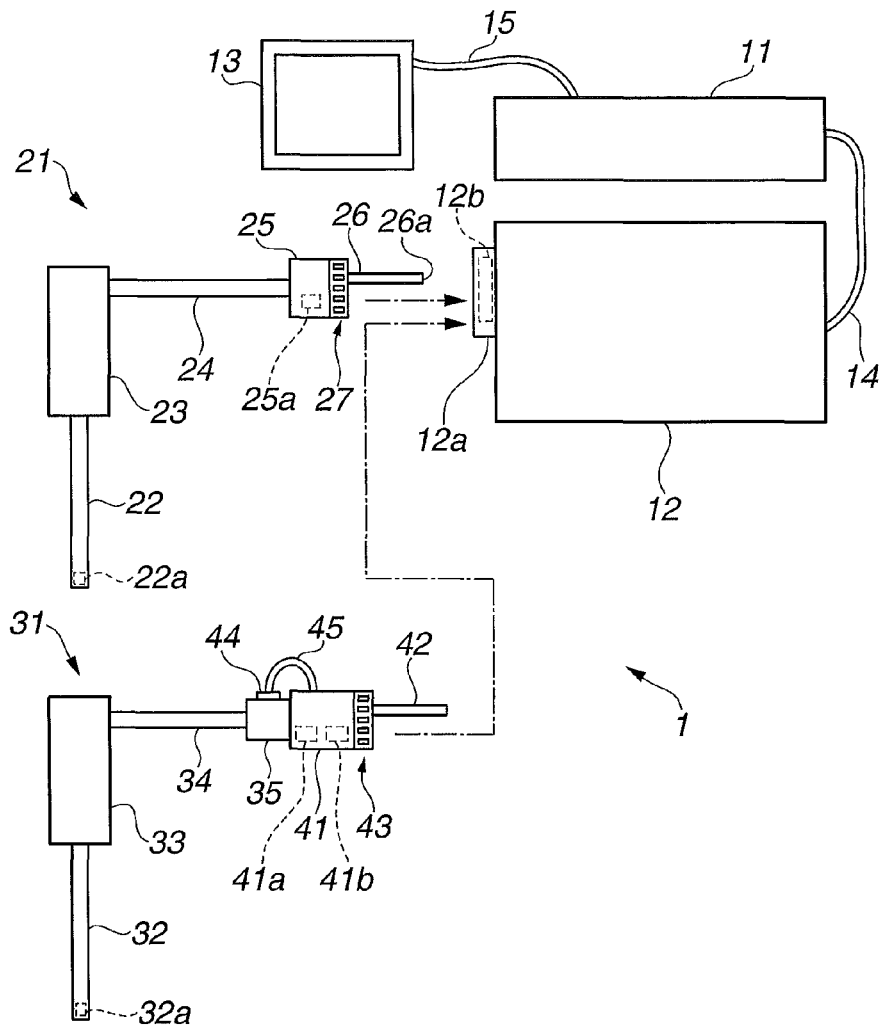
FIG. 1 is a configuration diagram showing a configuration of an endoscope system according to an embodiment of the present invention.

An embodiment of the present invention will be described below with reference to drawings.
(System Configuration)
FIG. 1 is a configuration diagram showing a configuration of an endoscope system according to the present embodiment. An endoscope system 1 includes a processor 11 which digital signals are inputted to or outputted from to perform image processing and the like, a light source apparatus 12, and a monitor 13 as a display apparatus. The processor 11 and the light source apparatus 12 are connected via a cable 14, and the processor 11 and the monitor 13 are connected via a cable 15. In the endoscope system 1 according to the present embodiment, two types of endoscopes 21 and 31 are connectable to the light source apparatus 12.

The endoscope 21 of the first type is configured to include a flexible or rigid insertion portion 22, an operation section 23, a cable 24 and a connector 25 connected to the proximal end of the cable 24. An image pickup device 22a is mounted inside the distal end portion of the insertion portion 22. The endoscope 21 is attachable to and detachable from a connector portion 12a of the light source apparatus 12 via the connector 25.

The connector 25 has a light guide 26, which is a protruding end portion of a light guide for illumination, and an electrical contact section 27 which includes multiple contact points for various electrical signals. The connector portion 12a has an electrical contact section 12b having multiple contact points, which corresponds to the contact section 27, and a light guide connector portion (not shown) for connecting a light guide 12c corresponding to the light guide 26.

Note that, though the connector 25 and the connector portion 12a also have connection portions for an air/water feeding function, the connection portions for air/water feeding are not shown, and description thereof is omitted.

The connector portion 12a is configured so that, when the connector 25 is connected to the connector portion 12a of the light source apparatus 12, illumination light from a lamp (not shown) in the light source apparatus 12 is condensed on an end face 26a of the light guide 26, and the contact section 27 of the connector 25 and the contact section 12b of the connector portion 12 are in contact with each other.

Therefore, when the connector 25 is connected to the connector portion 12a of the light source apparatus 12, light from the light source apparatus 12 passes through the light guide 26 of the connector 25 and a light guide inserted through the endoscope 21 and is radiated from the distal end of the insertion portion 22 as illumination light. Furthermore, by connecting the connector 25 to the connector portion 12a of the light source apparatus 12, driving control of the image pickup device 22a arranged at the distal end of the insertion portion 22 from the processor 11 and reception of an image signal, which is a video signal from the image pickup device 22a, at the processor 11 become possible via the contact section 27. Furthermore, an operation signal of the operation section 23 is also transmitted to the processor 11 via the contact section 27.

The endoscope 21 has a flash memory 25a, which is a nonvolatile memory for storing an identifier specific to the endoscope 21 (hereinafter referred to as endoscope ID information) and various parameter data for adjustment, for example, in the connector 25. The endoscope ID information may be stored in a ROM provided separately.

As described later, when the endoscope 21 is connected to the processor 11 for the first time, a user performs white balance adjustment, and, at that time, the processor 11 executes white balance processing, acquires various parameters for adjustment and stores the various parameters for adjustment into the flash memory 25a of the endoscope 21. At the same time, the processor 11 stores endoscope ID information about the endoscope 21 for which the white balance adjustment has been performed. Thus, when the endoscope 21 is connected, the processor 11 can read the endoscope ID information about the endoscope 21 and judge whether the endoscope 21 has been connected for the first time or has been already connected in the past, on the basis of the read endoscope ID information.

As described above, the connector 25 of the endoscope 21 can be connected to the light source apparatus 12 by a one-touch operation, and parameters for adjustment, such as a coefficient for white balance adjustment, are stored in the flash memory 25a of the endoscope 21. Then, when the endoscope 21 is connected to the processor 11 again, the processor 11 can generate a driving clock signal for driving the image pickup device 22a and perform image processing, using the parameters for adjustment stored in the flash memory 25a of the endoscope 21, and, therefore, the user need not perform adjustment work.

On the other hand, the endoscope 31 of the second type is configured to include an insertion portion 32, an operation section 33, a cable 34 and a connector 35 connected to the proximal end of the cable 34. An image pickup device 32a which analog signals are inputted to or outputted from is mounted inside the distal end portion of the insertion portion 32.

As described later, an adapter for endoscope (hereinafter referred to as an adapter) 41 is configured such that it is connectable to the connector 35 of the endoscope 31, and, therefore, the endoscope 31 can be detachably connected to the connector portion 12a of the light source apparatus 12 via the adapter 41 by fitting the adapter 41 to the connector 35. The adapter 41 includes a ROM 41a which stores ID information about the adapter 41 (hereinafter referred to as adapter ID information) and a flash memory 41b which is a nonvolatile memory capable of storing various parameters for adjustment.

The endoscope 31 of the second type also has endoscope ID information, but the endoscope 31 is an endoscope of a type which cannot store parameters for adjustment such as a coefficient for white balance adjustment, in combination with the processor 11. For example, the endoscope 31 of the second type is an old type of endoscope, and has originally been used being connected to another light source apparatus and another processor. That is, though the endoscope 31 of the second type is used in combination with another processor, it can be used in combination with the new processor 11 for the endoscope 21 of the first type by using the adapter 41.

(Adapter)

Figure 2:
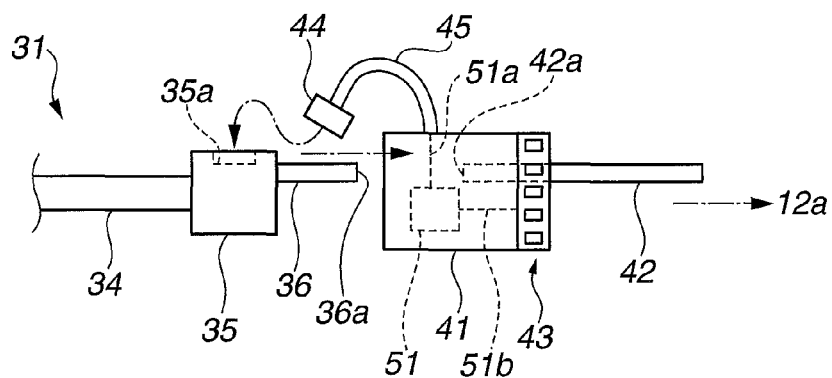
FIG. 2 is a diagram for illustrating a configuration of an adapter 41 according to the embodiment of the present invention.

FIG. 2 is a diagram for illustrating a configuration of the adapter 41. As shown in FIG. 2, the adapter 41 is configured such that it is connectable to the connector 35 of the endoscope 31. Furthermore, the adapter 41 is configured such that it is also connectable to the connector portion 12a of the light source apparatus 12. Therefore, the adapter 41 has a light guide 42, which is a protruding end portion of a light guide for illumination, and an electrical contact section 43 which includes multiple contact points for various electrical signals. That is, the adapter 41 is an adapter for endoscope which connects the endoscope 31 provided with the image pickup device 32a which analog signals are inputted to and outputted from and the processor 11 which digital signals are inputted to and outputted from.

The configuration of the contact section 43 is similar to that of the contact section 27 of the connector 25 of the endoscope 21.

The adapter 41 is configured such that, when the connector 35 is connected therewith, an end face 36a of a light guide 36 protruding on the proximal end side of the connector 35 is in contact with an end face 42a on the distal end side of the light guide 42 of the adapter 41. When the adapter 41 is connected to the connector portion 12a of the light source apparatus 12, illumination light from the lamp (not shown) in the light source apparatus 12 is condensed on the proximal end of the light guide 42. Therefore, the light guide 42 is a light transmission member which transmits light from the light source apparatus 12 to the light guide 36 of the endoscope 31.

Furthermore, the adapter 41 has an electrical connector 44 for connecting to an electrical connector 35a of the connector 35. The connector 44 is provided at the end portion of a cable 45 extended from the adapter 41.

Furthermore, the adapter 41 includes a circuit board 51 on which various circuits to be described later are mounted. The circuit board 51 is connected to the cable 45 via various signal lines 51a and connected to the contact section 43 via various signal lines 51b.

By connecting the adapter 41 to which the connector 35 is connected, to the connector portion 12a of the light source apparatus 12, light from the light source apparatus 12 passes through the light guide 42 of the adapter 41, the light guide 36 of the connector 35 and a light guide (not shown) inserted through the endoscope 31 and is irradiated from the distal end of the insertion portion 32 as illumination light. Furthermore, by connecting the adapter 41 to which the connector 35 is connected, to the connector portion 12a of the light source apparatus 12, the processor 11 can provide a driving signal to the image pickup device 32a arranged at the distal end of the insertion portion 32 and receive an image signal, which is a video signal from the image pickup device 32a, via the electrical connectors 35a and 44, the cable 45 and the contact section 43. Furthermore, an operation signal of the operation section 33 is also transmitted to the processor 11 via the contact section 43.

More specifically, by connecting the connector 35 of the endoscope 31 of the second type to the adapter 41, connecting the electrical connector 44 to the electrical connector 35a and fitting the adapter 41 to the connector portion 12a of the light source apparatus 12, the circuit board 51 and the endoscope 31 are connected via the various signal lines 51a, the cable 45, and the electrical connectors 44 and 35a, and, furthermore, the circuit board 51 and the processor 11 are connected via the various signal lines 51b, the contact sections 43 and 12b, and the cable 14.

As described above, the processor 11 can not only connect the endoscope 21 of the first type but also connect the endoscope 31 of the second type by using the adapter 41.

As described above, the endoscope 21 of the first type includes the flash memory 25a capable of storing ID information specific to the endoscope 21 of the first type and various parameters for adjustment inside the endoscope 21, and the processor 11 can read the information in the memory and write various parameters for adjustment.

Therefore, though the user is required to perform various adjustments such as white balance adjustment when he uses the endoscope 21 of the first type for the first time, he is not required to perform the various adjustments because the processor 11 reads the various parameter information for adjustment from the memory of the endoscope 21.

For example, when using multiple endoscopes 21 in combination with the processor 11, the user is required to perform various adjustments at the time of using each endoscope for the first time, but he does not have to perform any adjustment at all at the time of using the endoscope the second and succeeding times. Therefore, usability of using a combination of multiple endoscopes 21 and the processor 11 is good for the user.

As described above, though the endoscope 31 of the second type has ID information on the basis of a resistance value of a variable resistor or the like, the endoscope 31 is a type of endoscope which cannot store various parameters for adjustment in combination with the processor 11. The endoscope 31 of the second type is originally used in combination with another processor, it is necessary to perform various adjustment works each time of using the endoscope 31, and the processor has to acquire information about various parameters for adjustment, which is troublesome for the user.

In a hospital or the like where multiple endoscopes of the first type and multiple endoscopes of the second type are used, it is complicated from the viewpoint of operation to use processors corresponding to the different types, and, furthermore, it is troublesome for a user that the way of using is different between the two types.

By using the adapter 41 described above, however, the user can use the endoscope 31 of the second type with usability similar to that of the endoscope 21 of the first type.

Figure 3:
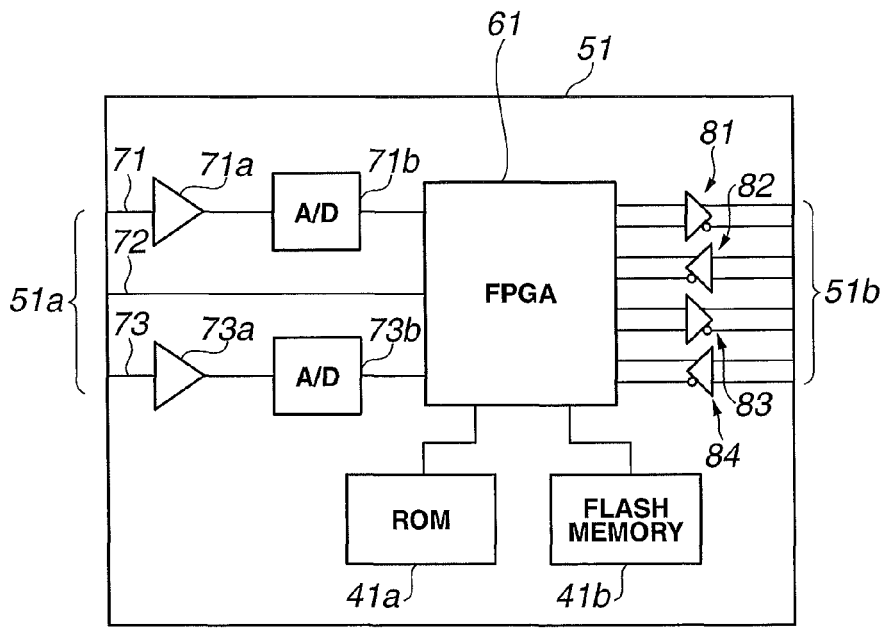
FIG. 3 is a block configuration diagram of a board 51 of the adapter 41 according to the embodiment of the present invention.

FIG. 3 is a block configuration diagram of the board 51 of the adapter 41. The board 51 includes a field programmable gate array (hereinafter referred to as an FPGA) 61 which executes various processes, the ROM 41a and the flash memory 41b.

The various signal lines 51a are connected to signal lines 71, 72 and 73 implemented on the board 51, respectively. The signal line 71 is a signal line for receiving an image signal from the image pickup device of the endoscope 31. The signal line 72 is a signal line for outputting a driving pulse signal which drives the image pickup device. The signal line 73 is a signal line for receiving an analog signal corresponding to endoscope ID information about the endoscope 31.

The board 51 includes: a buffer circuit 71a which is connected to the signal line 71 and which receives an image signal; an analog-digital converter (hereinafter referred to as an A/D converter) 71b connected to the buffer circuit 71a; a buffer circuit 73a which is connected to the signal line 73 and which receives an analog signal corresponding to endoscope ID information; and an A/D converter 73b connected to the buffer circuit 73a. The buffer circuit 73a, the A/D converter 73b and an I/F 96 constitute an endoscope identification information reception circuit which receives endoscope identification information, which is identification information about the endoscope 31.

Note that, when the endoscope ID information can be received from the endoscope 31 by a digital signal, the A/D converter 73b is unnecessary.

Furthermore, the various signal lines 51b are connected to a differential output circuit 81, a differential input circuit 82, a differential output circuit 83 and a differential input circuit 84 which are implemented on the board 51, respectively. The differential output circuit 81 is a circuit for outputting an image signal from the image pickup device 32a of the endoscope 31 to the processor 11 by a differential signal. The differential input circuit 82 is a circuit for inputting a driving clock signal from the processor 11 to the image pickup device 32a of the endoscope 31 by a differential signal. The differential output circuit 83 is a circuit for outputting data read from the ROM 41a and the flash memory 41b to the processor 11 by a differential signal. The differential input circuit 84 is a circuit for receiving various commands from the processor 11 and data from the processor 11 to be written into the flash memory 41b by a differential signal.

The FPGA 61 executes a process of converting a parallel image signal from the signal line 71 to a serial image signal and outputting the serial image signal to the differential output circuit 81 and a process of performing single conversion of a driving clock signal in a differential signal from the differential input circuit 82 to output a driving pulse signal.

Furthermore, the FPGA 61 executes a process of inputting ID information about the endoscope 31 and outputting the ID information to the differential output circuit 83, a process of converting endoscope ID information about the endoscope 31, adapter ID information in the ROM 14a and various parameters for adjustment in the flash memory 41b to serial signals and outputting the signals to the differential output circuit 83, according to a various information reading command from the differential input circuit 84, and a process of writing the various parameters for adjustment to the flash memory 41*b* according to a various information writing command from the differential input circuit 84.

Adapter ID information is stored in the ROM 41*a*. Therefore, the ROM 41*a* is an adapter identification information storage section which stores adapter identification information, which is identification information about the adapter 41.

Furthermore, in the ROM 41*a*, driving pulse generation information, such as the pulse period and voltage of a driving signal corresponding to the kind of the image pickup device 32*a* of the endoscope 31 of the second type, is stored. This is because the pulse period and the like of a driving signal differ according to the kind, specifications and the like of the image pickup device 32*a*.

Note that the kinds of the image pickup devices 32*a* mounted on the endoscopes 31 are such that the period, voltage and the like of a driving signal is the same, the adapter 41 may not hold the driving pulse generation information.

Note that the processor 11 may hold the driving pulse generation information so as to provide corresponding driving pulse generation information for the adapter 41 on the basis of endoscope ID information from the adapter 41.

The flash memory 41*b* stores various parameters for adjustment corresponding to a connected endoscope 31 as described later. More specifically, various parameters for adjustment for each of pieces of endoscope ID information about endoscopes 31 are stored in the flash memory 41*b*. Therefore, the flash memory 41*b* constitutes a parameter-for-adjustment storage section which stores parameters for adjustment.

Note that adapter ID information may be stored in the flash memory 41*b*.

Figure 4:
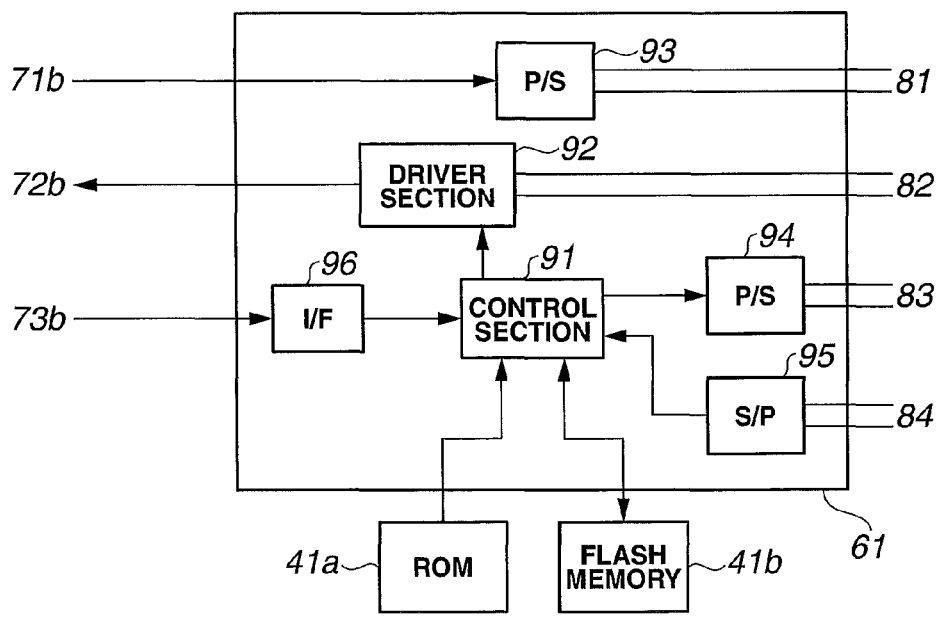
FIG. 4 is a block configuration diagram of an FPGA 61 according to the embodiment of the present invention.

FIG. 4 is a block configuration diagram of the FPGA 61.

The FPGA 61 includes a control section 91, a driver section 92, parallel-serial converters (hereinafter referred to as a P/S converters) 93 and 94, a serial-parallel converter (hereinafter referred to as an S/P converter) 95 and the interface (I/F) 96.

The control section 91 reads driving pulse generation information corresponding to the image pickup device 32*a* of the connected endoscope 31 on the basis of endoscope ID information to control the driver section 92.

The control section 91 performs a process of transmitting endoscope ID information about the endoscope 31, adapter ID information and various parameters for adjustment to the processor 11 according to a transmission request command from the processor 11 and performing writing to the flash memory 41*b* according to a various-parameters-for-adjustment writing request command from the processor 11.

Especially, when receiving a parameters-for-adjustment reading command from the processor 11, the control section 91 executes a process of reading parameters for adjustment corresponding to endoscope ID information about the connected endoscope 31 from the flash memory 41*b* and transmitting the parameters for adjustment to the processor 11.

Therefore, the control section 91 is a control section which performs control so as to store various parameters for adjustment received from the processor 11 into the flash memory 41*b* according to a parameters-for-adjustment writing command from the processor 11, and read the various parameters for adjustment stored in the flash memory 41*b* and output the parameters for adjustment to the processor 11 according to a various-parameters-for-adjustment reading command from the processor 11.

The driver section 92 is connected to the differential input circuit 82. The driver section 92 inputs a driving clock signal from the processor 11, performs single conversion of the signal and outputs a parallel driving pulse signal to the endoscope 31. The driver section 92 constitutes an image pickup device driving signal generation circuit which generates a driving pulse signal, which is a driving signal for driving the image pickup device 32*a*, on the basis of a driving clock signal, which is a driving control signal from the processor 11.

The P/S converter 93 is connected to the differential output circuit 81. The P/S converter 93 inputs a parallel image signal from the image pickup device 32*a*, converts the parallel signal to a serial signal and outputs the serial signal to the processor 11. Therefore, the A/D converter 73*b* and the P/S converter 93 constitute an image signal output circuit which converts an analog image signal from the image pickup device 32*a* to a digital image signal in a serial signal format and outputs the digital image signal to the processor 11.

The P/S converter 94 is connected to the differential output circuit 83. The control section 91 converts endoscope ID information, adapter ID information and various parameters for adjustment to serial signals and outputs the serial signals to the processor 11.

The S/P converter 95 is connected to the differential input circuit 84. The S/P converter 95 inputs various commands and various data from the processor 11, converts the commands and data to parallel signals and outputs the parallel signals to the control section 91.

(Processor Configuration)

Figure 5:
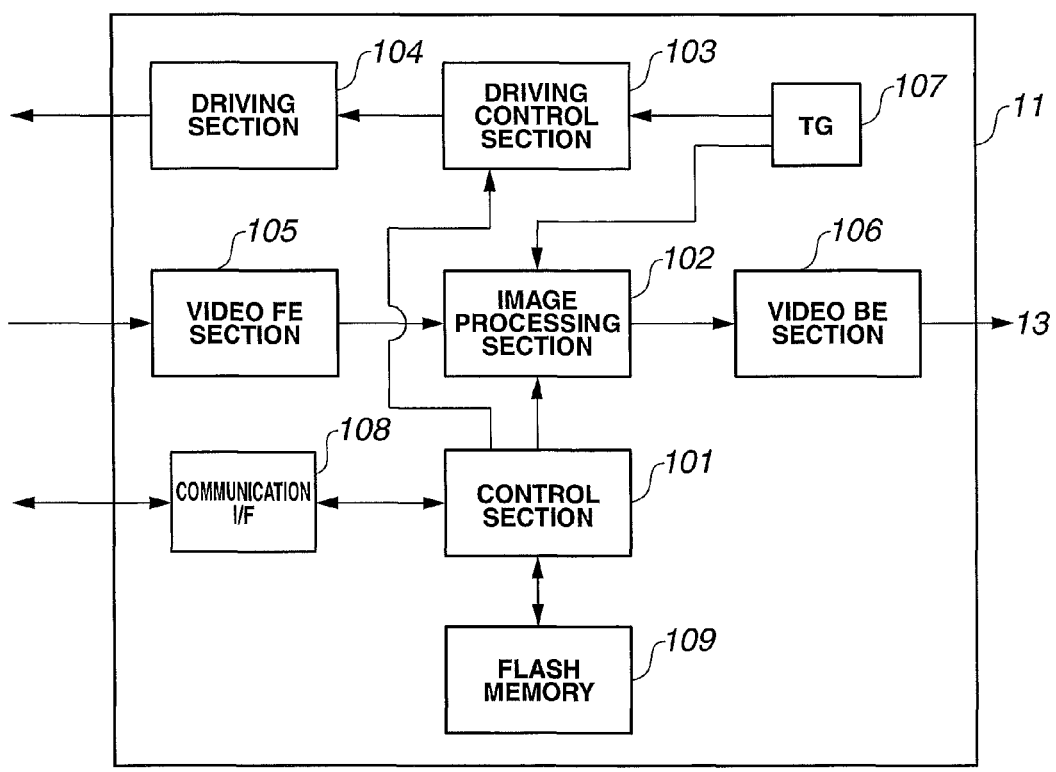
FIG. 5 is a block configuration diagram of a processor 11 according to the embodiment of the present invention.

FIG. 5 is a block configuration diagram of the processor 11.

The processor 11 is configured to include: a control section 101 having a central processing unit (hereinafter referred to as a CPU), an image processing section 102, a driving control section 103, a driving section 104, a video front end section (hereinafter referred to as a video FE section) 105, a video back end section (hereinafter referred to as a video BE section) 106, a timing generator (hereinafter referred to as a TG) 107, a communication interface (hereinafter referred to as a communication I/F) 108 and a flash memory 109 which is a nonvolatile memory.

The control section 101 controls the whole processor 11 so as to realize various functions of the endoscope system 1 corresponding to operation instructions by the user. A white balance adjustment function is included in the various functions. The control section 101 performs a process of controlling the image processing section 102 and the driving control section 103 on the basis of various parameters for adjustment obtained as a result of white balance processing.

The video FE section 105 receives an image signal of an endoscopic image received via the connector portion 12*a* of the light source apparatus 12 and provides the image signal to the image processing section 102.

The image processing section 102 performs predetermined image processing of the image signal from the video FE section 105 using various parameters for adjustment from the control section 101 and outputs the image-processed image signal to the video BE section 106. The video BE section 106 generates an analog image signal and outputs the analog image signal to the monitor 13.

The driving control section 103 generates a driving clock signal of each of image pickup devices of endoscopes using the various parameters for adjustment from the control section 101 and outputs the driving clock signal via the driving section 104.

The TG 107 generates various timing signals for the image processing section 102 and the driving control section 103.

The image processing section 102 and the driving control section 103 generate an image signal and a driving pulse signal, respectively, using the various timing signals from the TG 107.

The communication I/F 108 is an interface circuit for communication of various data such as an operation signal, endoscope ID information, adapter ID information and parameters for adjustment. The control section 101 performs data communication with the endoscope 21 and the adapter 41 via the communication I/F 108.

The flash memory 109 includes a table for storing adjusted endoscope information about endoscopes 21 of the first type and a table for storing adjusted combination information about combinations of endoscope 31 of the second type and adapter 41. Configurations of the tables will be described later.

(Parameter-for-Adjustment Acquisition Process and Writing Process)

Figure 6:
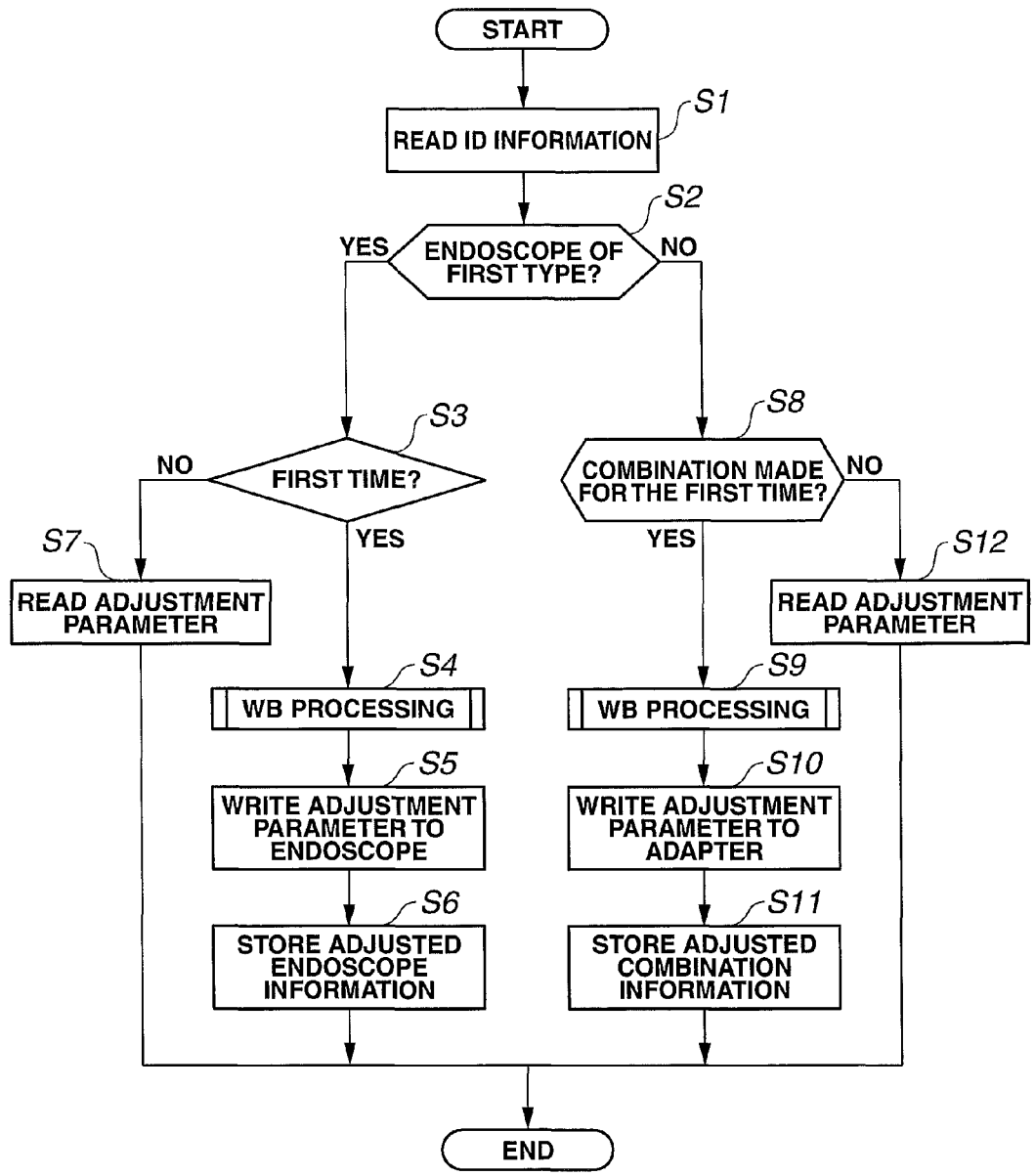
FIG. 6 is a flowchart showing an example of a flow of a parameter-for-adjustment acquisition and writing process of the processor 11, according to the embodiment of the present invention.

FIG. 6 is a flowchart showing an example of a flow of a parameter-for-adjustment acquisition and writing process of the processor 11.

When the processor 11 is powered on, the process in FIG. 6 is executed. The process in FIG. 6 is performed by the CPU of the control section 101 executing a predetermined program stored in a ROM or the like not shown. When the processor 11 is powered on, the processor 11 can receive a signal from the connector portion 12a of the light source apparatus 12.

When the processor 11 is powered on, the control section 101 outputs a predetermined command to read ID information in order to judge which of the endoscope 21 and the adapter 41 is connected to the connector portion 12a (S1). The reading of the ID information includes a case of reading endoscope ID information about the endoscope 21 and a case of reading adapter ID information about the adapter 41 and endoscope ID information about the endoscope 31.

If the endoscope 21 receives the command for reading ID information from the processor 11, the endoscope 21 reads endoscope ID information stored in the memory 25a and transmits the endoscope ID information to the processor 11. If the adapter 41 receives the command for reading ID information from the processor 11, the FPGA 61 transmits adapter ID information stored in the memory 41a to the processor 11. The FPGA 61 also reads the resistance value of a resistor for identification of the connected endoscope 31, via the buffer circuit 73a, converts the resistance value to a digital signal in the A/D converter 73b and transmits the digital signal to the processor 11 as endoscope ID information about the endoscope 31.

Note that the endoscope ID information about the endoscope 31 may be obtained by recording the endoscope ID information about the endoscope 31 to a ROM provided in the endoscope 31 and providing means for reading information in the ROM for the adapter 41.

Then, the control section 101 of the processor 11 judges whether the endoscope 21 of the first type is connected to the connector portion 12a or the endoscope 31 of the second type is connected via the adapter 41, on the basis of the received ID information (S2). That is, when receiving only endoscope ID information, the control section 101 judges that the endoscope 21 of the first type is connected; and, when receiving both of adapter ID information and endoscope ID information, the control section 101 judges that the endoscope 31 of the second type is connected.

Note that a code showing that only an endoscope is connected and a code showing that an endoscope and an adapter are connected may be stored in each of the endoscope 21 and the adapter 41 to judge whether a connected endoscope is the endoscope 21 of the first type or the endoscope 31 of the second type.

If it is judged that the endoscope 21 of the first type is connected (S2: YES), it is judged whether or not the endoscope 21 is an endoscope connected for the first time, on the basis of the endoscope ID information (S3). Since adjusted endoscope information showing that an endoscope is an endoscope 21 which has been connected in the past and for which white balance adjustment has been executed is stored in the flash memory 109 of the processor 11, the above judgment is performed on the basis of the information. The adjusted endoscope information stored in the flash memory 109 will be described later.

If the endoscope 21 is an endoscope connected for the first time or an endoscope for which white balance adjustment has not been executed yet (S3: YES), the control section 101 performs white balance (WB) processing (S4). In the white balance processing, white balance adjustment, gain adjustments among channels and the like are performed. The white balance processing is similar to conventional processing. Various parameters for adjustment obtained in the white balance processing include a coefficient for white balance adjustment, a coefficient for gain adjustment among channels and the like.

Then, the control section 101 writes the various parameters for adjustment obtained as a result of the white balance processing into the flash memory 25a of the endoscope 21 (S5), writes and stores the endoscope ID information into a table TBL1 (to be described later) in the flash memory 109 as adjusted endoscope information (S6), and ends the process.

If the endoscope 21 is not an endoscope connected for the first time (S3: NO), the control section 101 reads parameters for adjustment from the flash memory 25a of the endoscope 21 (S7) and ends the process.

After the processes of S6 and S7, the processor 11 is in a state capable of executing driving of the image pickup device and image processing of an image signal appropriately, using the various parameters for adjustment obtained by the white balance processing (S4) or read from the flash memory 25a (S7), and, therefore, the endoscope system 1 transitions to a state in which the user can perform endoscopy using the endoscope system 1.

If the endoscope is not an endoscope of the first type (S2: NO), it is judged whether or not the combination of endoscope 31 and adapter 41 is a combination made for the first time on the basis of the endoscope ID information and the adapter ID information (S8). Since adjusted combination information showing that a combination is a combination of endoscope 31 and adapter 41 which has been connected in the past and for which white balance adjustment has been executed is stored in the flash memory 109 of the processor 11, the above judgment is performed on the basis of the information. The adjusted combination information stored in the flash memory 109 will be described later.

If the combination of the endoscope 31 and the adapter 41 are a combination made for the first time (S8: YES), white balance processing similar to S4 is performed (S9).

Then, the control section 101 writes the various parameters for adjustment obtained as a result of the white balance processing into the flash memory 41b of the adapter 41 (S10), writes and stores the endoscope ID information and the adapter ID information into a table TBL2 (to be described later) in the flash memory 109 as adjusted combination information (S11), and ends the process.

If the combination of the endoscope 31 and the adapter 41 is not a combination made for the first time (S8: NO), the control section 101 reads parameters for adjustment for the combination from the flash memory 41b of the adapter 41 (S12) and ends the process. At that time, when receiving a parameters-for-adjustment reading command from the processor 11, the adapter 41 reads parameters for adjustment corresponding to endoscope ID information about the connected endoscope 31 and transmits the parameters to the processor 11.

After the processes of S11 and S12, the processor 11 is in a state capable of executing driving of the image pickup device 32a and image processing of an image signal appropriately, using the various parameters for adjustment obtained by the white balance processing (S9) or read from the flash memory 41b (S12), and, therefore, the endoscope system 1 transitions to a state in which the user can perform endoscopy using the endoscope system 1.

Therefore, the control section 101 is a processing section which judges existence or nonexistence of adjusted combination information about a combination of endoscope identification information and adapter identification information received from the adapter 41 by referring to the table TBL2 in the flash memory 109; if the adjusted combination information does not exist, executes predetermined adjustment processing, stores parameters for adjustment obtained by the execution into the flash memory 41b of the adapter 41 and stores adjusted combination information about the combination of the endoscope identification information and the adapter identification information into the table TBL2; and, if the adjusted combination information exists, reads parameters for adjustment stored in the memory 41b of the adapter 41.

Next, the adjusted endoscope information and the adjusted combination information will be described.

The flash memory 109 of the processor 11 stores two table data. One is a table for storing adjusted endoscope information about endoscopes 21 of the first type, and the other is a table for storing adjusted combination information about a combination of endoscope 31 of the second type and adapter 41.

FIG. 7 is a diagram showing a configuration of a table for storing adjusted endoscope information about endoscopes 21 of the first type. The table TBL1 stores endoscope ID information for which white balance processing has been executed at S4 and various parameter data for adjustment have been written into the flash memory 25a of the endoscope 21 at S5.

If judging that an endoscope 21 is connected (S2:YES), the control section 101 refers to the table TBL1 and checks whether endoscope ID information about the endoscope 21 exists or not. If the endoscope ID information exists in the table TBL1 as a result of the checking, it is judged that the endoscope 21 is an endoscope 21 for which white balance processing has been already executed. If the endoscope ID information does not exist in the table TBL1 as a result of the checking, it is judged that the endoscope 21 is an endoscope 21 connected and used for the first time.

FIG. 8 is a diagram showing a configuration of a table for storing adjusted combination information about endoscopes 31 of the second type and adapters 41. The table TBL2 stores information about combinations of endoscope ID information about endoscope 31 for which white balance processing has been executed at S9 and parameters for adjustment have been written into the flash memory 41b of the adapter 41 at S10 and adapter ID information about adapter 41.

If judging that an endoscope 31 is connected via an adapter 41 (S2: NO), the control section 101 refers to the TBL2 and checks whether a combination of adapter ID information about the adapter 41 and endoscope ID information about the endoscope 31 exists or not. If the combination of the adapter ID information and the endoscope ID information exists in the TBL2 as a result of the checking, it is judged that the combination is a combination of the adapter 41 and the endoscope 31 for which white balance adjustment has been already executed. If the combination of the adapter ID information and the endoscope ID information does not exist in the TBL2 as a result of the checking, it is judged that the combination is a combination of the adapter 41 and the endoscope 31 connected and used for the first time. Therefore, the TBL2 constitutes an adjusted combination information storage section which stores adjusted combination information showing whether predetermined adjustment processing has been performed or not for a combination of endoscope identification information and adapter identification information.

As described above, similarly to the case of using the endoscope 21 which stores various parameters for adjustment, such as a white balance coefficient, in a built-in nonvolatile memory, the user can use the endoscope 31 which does not include such a memory, by using the adapter 41 without performing white balance adjustment each time he uses the endoscope 31.

Note that, even in the case where, in a combination of the endoscope 21 and the processor 11, an endoscope having a nonvolatile memory capable of storing only a part of parameters for adjustment to be stored into the flash memory 25a of the endoscope 21 is connected, it is possible to store parameters for adjustment which cannot be stored in the endoscope 21 or all parameters for adjustment required for combination with the processor 11 into the flash memory 41b of the adapter 41 by causing the adapter 41 to intervene. Therefore, the endoscope can be used with usability similar to that of the endoscope 21 of the first type.

(Variation)

Next, a variation of the adapter 41 will be described.

In the adapter 41 described above, the adapter body has the light guide 42 and the contact section 43 so that the adapter 41 is adapted to the light source apparatus 12 compatible with the endoscope 21 of the first type. However, the adapter 41 may be used in combination of the processor 11 compatible with the endoscope 21 of the first type and a light source apparatus compatible with the endoscope 31 of the second type. To cope with such a case, the adapter may be such that is used only for connection to the electrical connector of the endoscope 31 of the second type.

Figure 9:
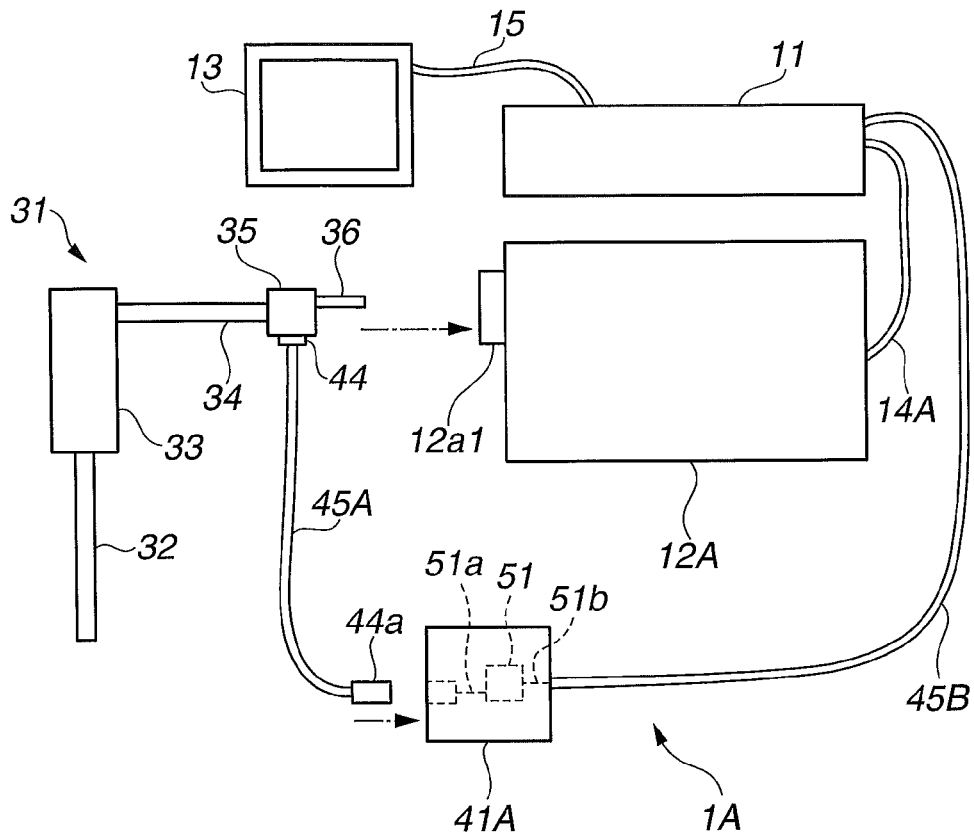
FIG. 9 is a diagram for illustrating a configuration example of an endoscope system 1A using an adapter 41A according to a variation of the embodiment of the present invention.
Figure 10:
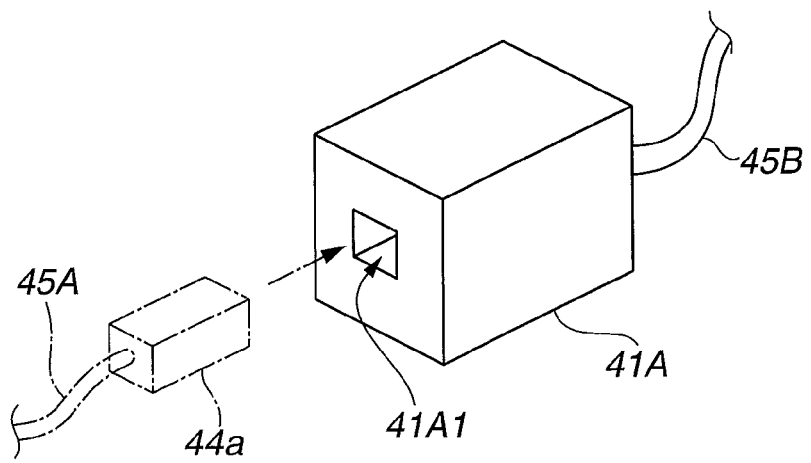
FIG. 10 is a perspective view of the adapter 41A according to the variation of the embodiment of the present invention.

FIG. 9 is a diagram for illustrating a configuration example of an endoscope system 1A using an adapter 41A according to the present variation. FIG. 10 is a perspective view of the adapter 41A. Note that, in FIG. 9, the same components as those in the above embodiment are given the same reference numerals, and description thereof is omitted.

The endoscope system 1A is configured with the processor 11, a light source apparatus 12A, an adapter 41A and the endoscope 31 of the second type. The light source apparatus 12A is a light source apparatus compatible with the endoscope 31, and the light guide 36 of the endoscope 31 can be fitted to a connector portion 12a1. The connector 12a1 supplies illumination light to the light guide 36. The light source apparatus 12A is connected to the processor 11 via a cable 14A and can receive a control signal from the processor 11.

The adapter 41A is in a box shape and is connectable to the connector 35 of the endoscope 31 via a cable 45A. The adapter 41A is connectable to the processor 11 via a cable 45B extended from the adapter 41A. The adapter 41A includes the circuit board 51.

The cable 45A has a connector 44a at one end. By inserting and fitting the connector 44a into a slot 41A1 of the adapter 41A, a contact section of the connector 44a is electrically connected to a contact section of the adapter 41A, and the connector 35a and the circuit board 51 are electrically connected.

Therefore, the processor 11 and the endoscope 13 can exchange electrical signals via the adapter 41A, and the circuit board 51 can receive various commands from the processor 11 and transmit endoscope ID information about endoscope 31, and the like. Furthermore, the processor 11 can provide a driving signal to the image pickup device 32a and receive an image signal from the image pickup device 32a via the circuit board 51.

Thus, according to the configuration as shown in FIG. 9 also, the user can use the endoscope 31 of the second type with usability similar to that of an endoscope of the first type, using the processor 11 compatible with the endoscope 21 of the first type.

As described above, according to the embodiment and variation described above, an adapter for endoscope, a processor for endoscope and an endoscope system can be realized which enable the user to use the endoscope connected to the processor, using the adapter with usability similar to the usability in the case of using an endoscope which stores various parameters for adjustment in its built-in nonvolatile memory.

The present invention is not limited to the embodiment described above, and various modifications, alterations and the like are possible within a range not departing from the spirit of the present invention.

What is claimed is:

1. An adapter for endoscope connecting an endoscope provided with an image pickup device which analog signals are inputted to and outputted from and a processor which digital signals are inputted to and outputted from, the adapter comprising:
   an image pickup device driving signal generation circuit generating a driving signal for driving the image pickup device on the basis of a driving control signal from the processor;
   an image signal output circuit converting an analog image signal from the image pickup device to a digital image signal in a serial signal format and outputting the digital image signal to the processor;
   an endoscope identification information reception circuit receiving endoscope identification information which is identification information about the endoscope;
   an adapter identification information storage section storing adapter identification information which is identification information about the adapter for endoscope;
   an information transmission section transmitting the endoscope identification information and the adapter identification information to the processor;
   a parameter-for-adjustment storage section storing parameters for adjustment; and
   a control section performing control to store the parameters for adjustment received from the processor into the parameter-for-adjustment storage section according to a command to write the parameters for adjustment from the processor which is configured to receive the endoscope identification information and the adapter identification information, and read the parameters for adjustment stored in the parameter-for-adjustment storage section according to a command to read the parameters for adjustment from the processor and output the parameters for adjustment to the processor.

2. The adapter for endoscope according to claim 1, wherein the parameter-for-adjustment storage section stores the parameters for adjustment for each piece of the endoscope identification information; and
   when receiving the reading command, the control section reads the parameters for adjustment stored in the parameter-for-adjustment storage section on the basis of the endoscope identification information and outputs the parameters for adjustment to the processor.

3. The adapter for endoscope according to claim 1, further comprising a light transmission member transmitting light from a light source apparatus to a light guide of the endoscope.

4. The adapter for endoscope according to claim 1, wherein the parameters for adjustment include a coefficient for white balance adjustment and a coefficient for gain adjustment among channels.

5. A processor capable of inputting and outputting digital signals to and from an adapter for endoscope to which an endoscope is connectable, the endoscope being provided with an image pickup device which analog signals are inputted to and outputted from, wherein
   the adapter for endoscope comprises:
   an image pickup device driving signal generation circuit generating a driving signal for driving the image pickup device on the basis of a driving control signal from the processor;
   an image signal output circuit converting an analog image signal from the image pickup device to a digital image signal in a serial signal format and outputting the digital image signal to the processor;
   an endoscope identification information reception circuit receiving endoscope identification information which is identification information about the endoscope;
   an adapter identification information storage section storing adapter identification information which is identification information about the adapter for endoscope;
   an information transmission section transmitting the endoscope identification information and the adapter identification information to the processor;
   a parameter-for-adjustment storage section storing parameters for adjustment; and
   a control section performing control to store the parameters for adjustment received from the processor into the parameter-for-adjustment storage section according to a command to write the parameters for adjustment from the processor which is configured to receive the endoscope identification information and the adapter identification information, and read the parameters for adjustment stored in the parameter-for-adjustment storage section according to a command to read the parameters for adjustment from the processor and output the parameters for adjustment to the processor; and
   the processor comprises:
   an adjusted combination information storage section storing adjusted combination information showing whether predetermined adjustment processing has been performed or not for a combination of the endoscope identification information and the adapter identification information; and
   a control section judging existence or nonexistence of the adjusted combination information about a combination of the endoscope identification information and the adapter identification information received from the adapter for endoscope by referring to the adjusted combination information storage section; if the adjusted combination information does not exist, executing the predetermined adjustment processing, storing the parameters for adjustment obtained by the execution into the parameter-for-adjustment storage section of the adapter for endoscope and storing the adjusted combination information about the combination of the endoscope identification information and the adapter identification information into the adjusted combination information storage section; and, if the adjusted combination information exists, reading the parameters for adjustment stored in the parameter-for-adjustment storage section of the adapter for endoscope.

6. The processor for endoscope according to claim 5, wherein the parameters for adjustment include a coefficient for white balance adjustment and a coefficient for gain adjustment among channels.

7. An endoscope system comprising:
an adapter for endoscope to which an endoscope is connectable, the endoscope being provided with an image pickup device which analog signals are inputted to and outputted from; and
a processor which digital signals are inputted to and outputted from, wherein
the adapter for endoscope comprises:
an image pickup device driving signal generation circuit generating a driving signal for driving the image pickup device on the basis of a driving control signal from the processor;
an image signal output circuit converting an analog image signal from the image pickup device to a digital image signal in a serial signal format and outputting the digital image signal to the processor;
an endoscope identification information reception circuit receiving endoscope identification information which is identification information about the endoscope;
an adapter identification information storage section storing adapter identification information which is identification information about the adapter for endoscope;
an information transmission section transmitting the endoscope identification information and the adapter identification information to the processor;
a parameter-for-adjustment storage section storing parameters for adjustment; and
a control section performing control to store the parameters for adjustment received from the processor into the parameter-for-adjustment storage section according to a command to write the parameters for adjustment from the processor which is configured to receive the endoscope identification information and the adapter identification information, and read the parameters for adjustment stored in the parameter-for-adjustment storage section according to a command to read the parameters for adjustment from the processor and output the parameters for adjustment to the processor; and
the processor comprises:
an adjusted combination information storage section storing adjusted combination information showing whether predetermined adjustment processing has been performed or not for a combination of the endoscope identification information and the adapter identification information; and
a control section judging existence or nonexistence of the adjusted combination information about a combination of the endoscope identification information and the adapter identification information received from the adapter for endoscope by referring to the adjusted combination information storage section; if the adjusted combination information does not exist, executing the predetermined adjustment processing, storing the parameters for adjustment obtained by the execution into the parameter-for-adjustment storage section of the adapter for endoscope and storing the adjusted combination information about the combination of the endoscope identification information and the adapter identification information into the adjusted combination information storage section; and, if the adjusted combination information exists, reading the parameters for adjustment stored in the parameter-for-adjustment storage section of the adapter for endoscope.

8. The endoscope system according to claim 7, wherein the parameters for adjustment include a coefficient for white balance adjustment and a coefficient for gain adjustment among channels.

9. The endoscope system according to claim 7, further comprising a light source apparatus for supplying illumination light to the endoscope.

* * * * *